United States Patent [19]

Formanek et al.

[11]  4,435,601
[45]  Mar. 6, 1984

[54] PREPARATION OF POLYPHENOLS BY OXIDATION OF HYDROXYBENZALDEHYDES

[75] Inventors: Karel Formanek, Serezin Du Rhone; Daniel Michelet, Tassin La Demi-Lune; Dominique Petre, Lyons, all of France

[73] Assignee: Rhone-Poulenc Industries, Paris, France

[21] Appl. No.: 281,248

[22] Filed: Jul. 7, 1981

[30] Foreign Application Priority Data

Jul. 11, 1980 [FR] France .................. 80 15753

[51] Int. Cl.³ ............................................. C07C 45/64
[52] U.S. Cl. ............................. 568/430; 568/424; 568/706; 568/746; 568/764; 568/765; 568/766; 568/649; 568/650; 568/651; 568/771
[58] Field of Search ............ 568/430, 433, 764, 432, 568/442, 424, 706, 746, 765, 766, 771, 649, 650, 651

[56] References Cited

U.S. PATENT DOCUMENTS

| | | | |
|---|---|---|---|
| 1,891,149 | 12/1932 | Elger | 568/430 |
| 1,965,458 | 7/1934 | Elger . | |
| 4,119,671 | 10/1978 | Bauer et al. | 568/432 |
| 4,190,605 | 2/1980 | Muench et al. | 568/432 |
| 4,205,188 | 5/1980 | Muench et al. | 568/432 |

FOREIGN PATENT DOCUMENTS 2075617 10/1971 France .

OTHER PUBLICATIONS

Patai, The Chemistry of the Carbonyl Group (1966), 749–753, 758–759.
Martin, J.A.C.S., vol. 74, (1952), 3024–3025.
Freeman et al., J.A.C.S., vol. 76, (1954), 2080–2087.

Primary Examiner—Bernard Helfin
Attorney, Agent, or Firm—Burns, Doane, Swecker & Mathis

[57] ABSTRACT

Optionally aldehyde substituted polyphenols are prepared by oxidizing, with hydrogen peroxide, a hydroxybenzaldehyde bearing at least one aldehyde substituent ortho- and/or para- to the nuclear hydroxyl group, in an aqueous reaction medium and in the presence of an alkali or alkaline earth metal base, the process being characterized in that the pH of the reaction medium is continuously maintained at a value no greater than 7 throughout the course of the oxidation reaction.

The subject process is well suited for the preparation of, e.g., hydroxy-p-vanillin from guaiacol, and the novel compound 2,4,6-triformylphenol.

36 Claims, No Drawings

PREPARATION OF POLYPHENOLS BY OXIDATION OF HYDROXYBENZALDEHYDES

BACKGROUND OF THE INVENTION

1. Field of the Invention

The present invention relates to the preparation of "polyphenols", i.e., phenolic compounds containing at least two nuclear hydroxyl groups and optionally one aldehyde group, and, more especially, to the preparation of such polyphenols by oxidation of hydroxybenzaldehydes with hydrogen peroxide.

2. Description of the Prior Art

Polyphenols, whether unsubstituted or substituted with functional groups such as aldehyde and/or alkoxy groups, are in wide demand as industrial products. Thus, hydroquinone is widely used, in particularly, in the photographic industry. Pyrocatechol is in turn a particularly important raw material for the preparation of certain organic compounds, such as guaiacol and its derivatives, or for the preparation of resins by condensation with formaldehyde. Pyrogallol is also employed as a photographic developer and as an intermediate in various organic syntheses. Likewise as regards protocatechaualdehyde (3,4-dihydroxybenzaldehyde), hydroxy-para-vanillin (3,4-dihydroxy-5-methoxybenzaldehyde) and hydroxy-ortho-vanillin (2,5-dihydroxy-3-methoxybenzaldehyde).

And numerous processes for the preparation of polyphenols have to date been proposed to this art. Among such processes, two types in particular have in common the oxidation of a phenolic compound with hydrogen peroxide and the peroxides derived therefrom, and especially inorganic or organic peracids.

The aforesaid two types of processes differ in the nature of the starting materials. Thus, it is known to prepare polyphenols by direct hydroxylation of the aromatic nucleus with hydrogen peroxide or organic peracids such as performic and peracetic acids. Hydroxylation processes of this type, which are especially suited for the preparation of hydroquinone and pyrocatechol have been described, in particular, in U.S. Pat. Nos. 3,514,490, 3,849,502 and 4,208,536. Although these processes have proven to be of great value, it is advantageous in certain instances to use a second group of processes, the characteristic of which is the substitution of one or more aldehyde groups of a benzaldehyde by one or more hydroxyl groups.

The oxidation of aromatic aldehydes to the corresponding phenols by means of hydrogen peroxide or percarboxylic acids, which is generally known as the Bayer and Villiger reaction, is a convenient means of obtaining a phenol, if a source of aromatic aldehydes is available (compare C. H. Hassal, *Organic Reactions,* Volume 9, pages 73 to 106 (1957)). The Bayer and Villiger reaction actually entails two types of reaction. The first consists of the oxidation of aromatic aldehydes with percarboxylic acids formed "in situ" or prepared for immediate use by reacting hydrogen peroxide with a carboxylic acid such as formic, acetic or benzoic acids. In all cases, this oxidation can be carried out in the presence of a strong acid as a catalyst (for example, toluenesulfonic acid). Not all aromatic aldehydes yield phenols according to this reaction. In fact, it has been found that benzaldehyde and its homologs containing electron-attracting substituents (for example, halogen atoms or the nitro group) are oxidized by peracids to the corresponding benzoic acids, while aromatic aldehydes containing electron-donating substituents (hydroxyl, alkoxy or alkyl groups), such as salicylaldehyde, p-hydroxybenzaldehyde and ortho- and p-methoxybenzaldehydes, give rise to the corresponding phenols (if appropriate in the form of formates, depending on the reaction conditions) (compare J. Boeseken et al, *Rec. Trav. Chim. Pays-Bas,* 55, 815 (1936); J. Boeseken et al, *Ibid.,* 74, 845 (1941); and Y. Ogata et al, *J. Org. Chem.,* 26, 4,803 (1961)). This process of oxidation of aromatic aldehydes containing electron-donating substituents to phenols exhibits the disadvantage in that it requires the use of a carboxylic acid, which in fact acts as an active-oxygen carrier in the reaction. The presence of the carboxylic acid in the process mandates the use of large reaction volumes, which limits the productivity of the reaction on an industrial scale. Furthermore, the fact that the reaction is carried out in an anhydrous medium, in order to assist the formation of the peracids, creates explosion hazards. It is thus desirable to dispense with the use of any carboxylic acid and consequently to use hydrogen peroxide directly as the source of active oxygen. This object is achieved by carrying out the reaction in an alkaline medium, and this constitutes the second group of processes classed as the Bayer and Villiger reaction, and generally designated as the Dakin reaction. According to Dakin (compare *Amer. Chem. J.,* 42, 474 (1909)), aromatic aldehydes containing one or more hydroxyl groups in the ortho- or para-position to the carbonyl group are oxidized in good yields to the corresponding polyphenols by hydrogen peroxide in an alkaline medium. Under these conditions, the aldehyde groups in the meta-position to the phenolic hydroxyl are not oxidized. This process has been applied to numerous aromatic aldehydes containing at least one hydroxyl group in the ortho- or para-position, such as, in particular, salicylaldehyde, p-hydroxybenzaldehyde, 2,4-dihydroxybenzaldehyde, 2-hydroxy-3-methoxybenzaldehyde, 2-hydroxy-5-methoxybenzaldehyde and 3-hydroxy-5-methoxybenzaldehyde. Distinct from the Bayer and Villiger reaction itself, the Dakin reaction applies to hydroxybenzaldehydes substituted by halogen atoms, such as 3,5-dibromo-4-hydroxybenzaldehyde, 3,5-dichloro-4-hydroxybenzaldehyde, 5-bromo-2-hydroxybenzaldehyde and 3-bromo-4-hydroxy-5-methoxybenzaldehyde, and to certain nitrohydroxybenzaldehydes, such as 3-nitro-2-hydroxybenzaldehyde, 5-nitro-2-hydroxybenzaldehyde and 2-nitro-4-hydroxy-3-methoxybenzaldehyde (compare Dakin loc. cit.; Dakin, *Org. Synth. Coll.,* Volume 1, page 149 (1941); Surrey, *Org. Synth.,* 26, page 90 (1946); and J. Kvalnes, *J. Amer. Chem. Soc.,* 56, 2,487 (1934)).

The Dakin reaction is carried out in an aqueous solution of an alkali metal base, such as sodium hydroxide, the pH of the medium being strongly alkaline and characteristically, above 8. Under these conditions, it is impossible to avoid undesirable oxidation of the reaction products to quinones. Furthermore, it has been found that, in the case of hydroxybenzaldehydes containing both an aldehyde group in the para-position and at least one aldehyde group in the ortho-position to the phenolic hydroxyl, the yields of products resulting only from the oxidation of the aldehyde groups in the ortho-position are low in an alkaline medium, even if the amount of hydrogen peroxide is insufficient to oxidize all the aldehyde groups present. It is therefore impossible, under the usual conditions of the Dakin reaction, to prepare polyhydroxybenzaldehydes with yields high enought to be of industrial value by oxidizing only the aldehyde groups in the ortho-position to the phenolic hydroxyl. This is the case as regards the oxidation of 2-hydroxy-3-methoxyisophthaldehyde (diformylguaiacol) to ortho-hydroxy-p-vanillin. In the same way, it can prove advantageous on an industrial scale to be able to oxidize, with good yields, a mixture of an ortho-hydroxybenzaldehyde and a para-hydroxybenzaldehyde, such as a mixture of salicylaldehyde and p-hydroxybenzaldehyde, or a mixture of vanillin and 2-hydroxy-3-methoxybenzaldehyde.

SUMMARY OF THE INVENTION

Accordingly, a major object of the present invention is the provision of an improved process for the oxidation of hydroxybenzaldehydes to polyphenols with hydrogen peroxide, consistent with the Dakin reaction, but which improved process does not exhibit the disadvantages and drawbacks to date characterizing the state of the prior art.

Briefly, the present invention features a process for the preparation of polyphenols, optionally comprising a nuclear aldehyde function, by the oxidation of hydroxybenzaldehydes containing at least one aldehyde group in the ortho- and/or para-position to the hydroxyl group, with hydrogen peroxide, in an aqueous medium, in the presence of an alkali metal base or alkaline earth metal base, characterized in that the pH of the reaction medium is less than or equal to 7 completely throughout the reaction.

DETAILED DESCRIPTION OF THE INVENTION

More particularly according to this invention, it has now unexpectedly been found that by continuously maintaining the pH of the reaction medium at a value which is no greater than 7, it is thus possible to avoid, or at least to limit, for all of the hydroxybenzaldehydes consumed, the oxidation to quinones by means of the hydrogen peroxide, of the polyphenols formed over the course of the reaction. The subject invention also enables limitation of the degradation of the hydrogen peroxide to molecular oxygen and, consequently, limitation on the loss of active oxygen. In the case of hydroxybenzaldehydes simultaneously containing at least one aldehyde group in the ortho-position and one aldehyde group in the para-position to the phenolic hydroxyl, the process according to the invention is well adapted for the preparation, in excellent yields, of polyphenols having at least one nuclear hydroxyl group in the ortho-position and one nuclear aldehyde group in the para-position to the original hydroxyl. Finally, the process according to the invention enables oxidation of mixtures of ortho-hydroxybenzaldehydes and para-hydroxybenzaldehydes, while at the same time realizing those advantages noted hereinabove.

The choice of the optimum pH of the aqueous phase for the oxidation depends on the nature of the hydroxybenzaldehyde used. Indeed, to ensure a normal course of the Dakin reaction, it is preferred that the sparingly water-soluble hydroxybenzaldehyde be present in the aqueous phase in the form of its alkali metal or alkaline earth metal salt, or, more exactly, for the hydroxybenzaldehyde in the form of its salt to be continuously available in the aqueous phase without the pH of the latter thereby exceeding the limit of 7. Briefly, this optimum pH depends on the pKa of the particular hydroxybenzaldehyde in water. It is self-evident that the reaction still gives rise to the desired results if the pH value deviates somewhat to either side of the value corresponding to the pKa of the particular hydroxybenzaldehyde, provided, of course, that the limiting value of 7 is not exceeded. Thus, the pH can be below the optimum value corresponding to the pKa of the hydroxybenzaldehyde. However, it is found that the more acid the pH, the slower the reaction. Thus, it is not recommended to carry out the reaction at a pH below 2, although it remains within the scope of the present invention to carry out the reaction at a pH below this value.

Typically, a value ranging from 2 to 7, and preferably ranging from 3 to 6, throughout the reaction, is selected as the pH of the oxidation medium.

In practice, the pH of the aqueous phase containing the hydroxybenzaldehyde is adjusted to the desired value and the hydrogen peroxide is then added. To avoid a progressive drop in the pH, due to the formation of formic acid, an amount of an alkali metal base or alkaline earth metal base which is sufficient to avoid excessive acidification of the reaction medium is preferably added progressively as the reaction proceeds. In general, the amount of alkali metal base is calculated such as to maintain the pH in the region of the selected optimum value.

The process according to the invention is generally applicable to the oxidation of any hydroxybenzaldehydes containing at least one aldehyde group in the ortho- and/or para-position to a phenolic hydroxyl.

More specifically, it is very particularly suitable for the oxidation of the hydroxybenzaldehydes having the structural formula:

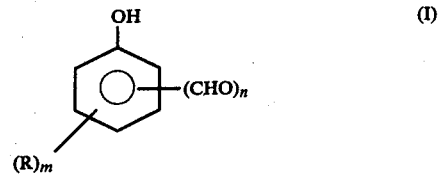

in which: n is an integer from 1 to 3, R represents an alkyl, alkoxy, hydroxyalkyl, cycloalkyl, aryl, alkoxyalkyl or hydroxyl radical, a nitro group or a halogen atom, and m is an integer from 0 to 3, the sum m+n being equal to at most 4 and preferably at most 3, which hydroxybenzaldehydes contain at least one aldehyde group in the ortho- and/or para-position.

More specifically, R represents an alkyl radical having from 1 to 20 carbon atoms, such as the methyl, ethyl, n-propyl, isopropyl, n-butyl, iso-butyl, t-butyl, pentyl, decyl and pentadecyl radicals; an alkoxy radical having from 1 to 20 carbon atoms, such as the methoxy, ethoxy, n-propoxy, isopropoxy, n-butoxy, t-butoxy, pentoxy, dodecyloxy and hexadecyloxy radicals; a cycloalkyl radical such as the cyclopentyl and cyclohexyl radicals; an aryl radical such as the phenyl, tolyl and xylyl radicals; an alkoxyalkyl radical having from 1 to 20 carbon atoms in total, such as the β-methoxyethyl, β-ethoxyethyl and 3-methoxy-n-propyl radicals; or a halogen atom such as chlorine and bromine.

Preferably, in the formula (I), R represents a lower alkyl radical containing from 1 to 4 carbon atoms, a lower alkoxy radical containing from 1 to 4 carbon atoms or a hydroxyl group, m is 0 or 1 and, even more preferably, n is equal to 2 or 3.

The process according to the present invention thus facilely provides, starting from the hydroxybenzaldehydes of the formula (I) and with the advantages noted hereinabove, for the preparation of those polyphenols containing at least one hydroxyl group more than the starting material compound subjected to oxidation, and, if appropriate, a residual aldehyde group in the para-position to the initial phenolic hydroxyl.

More specifically, the present invention features a process for the preparation of polyphenols optionally containing an aldehyde group, of the structural formula:

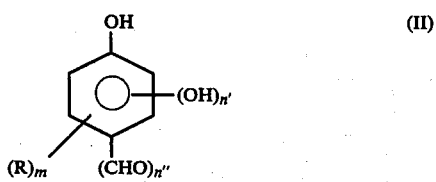

in which: R and m are as defined above, n' is an integer from 1 to 2 and n" is 0 or 1, the sum n'+n" being equal to n, the hydroxyl groups generated during the oxidation being in the ortho-position or, if appropriate, in the para-position to the initial phenolic hydroxyl.

Among the hydroxybenzaldehydes of the formula (I) to which the process according to the invention can be applied, a distinction is drawn between the following families:

(a) The hydroxybenzaldehydes containing one or two aldehyde groups directly attached to the nucleus and in the ortho-position to the phenolic hydroxyl, corresponding to the structural formula:

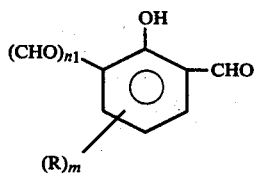

in which R and m are as defined above and $n_1$ is 0 or 1. Same give rise to the preparation of polyphenols of the structural formula:

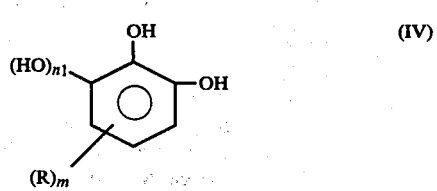

in which R and m are as defined above.

In the description which follows, the various symbols R, m, $n_1$, n' and n" used for the formulae (I) to (IV) will retain the definitions given above, unless indicated otherwise.

(b) The hydroxybenzaldehydes containing an aldehyde group in the para-position to the phenolic hydroxyl, of the structural formula:

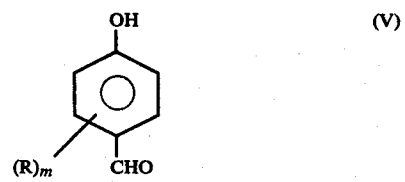

These particular hydroxybenzaldehydes give rise to the corresponding para-diphenols.

The process according to the present invention is applied with very marked success to the oxidation of mixtures of aldehydes of the formulae (III) and (V), such as those obtained by the hydroxymethylation of phenol or substituted phenols by means of formaldehyde or its derivatives, followed by oxidation of the mixtures of hydroxymethylphenols thus obtained. Salicylaldehyde/p-hydroxybenzaldehyde mixtures are particularly notable in this respect.

The subject process is also particularly suitable for the oxidation of the hydroxybenzaldehydes of the formulae (III) and (V) in which R represents a hydroxyl group or a lower alkoxy radical and m is equal to at least 1, and of their mixtures, such as protocatechualdehyde, 2,3-dihydroxybenzaldehyde, vanillin, ortho-vanillin, ethyl-vanillin, ortho-ethylvanillin, and protocatechualdehyde/2,3-dihydroxybenzaldehyde and vanillin/ortho-vanillin mixtures. During the oxidation of such mixtures, the use of a pH below 7 makes it possible to improve the yields of polyphenols derived from these hydroxybenzaldehydes, by substantial proportions.

(c) The hydroxybenzaldehydes containing both one or two aldehyde groups directly attached to the nucleus and in the ortho-position to the phenolic hydroxyl, and an aldehyde group in the para-position. These hydroxybenzaldehydes, which correspond more specifically to the structural formula:

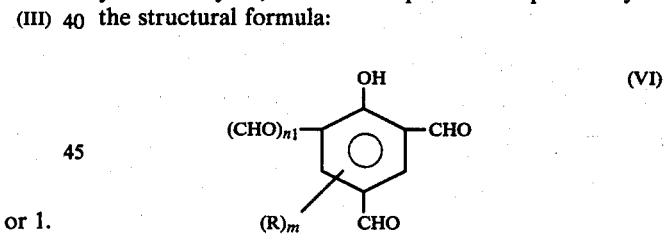

give rise to the preparation of polyhydroxybenzaldehydes of the general formula:

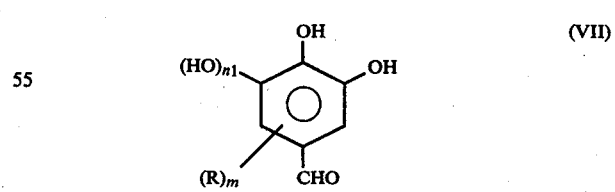

The process according to the present invention is especially suitable for the preparation of the polyhydroxybenzaldehydes of the formula (VII) from the hydroxybenzaldehydes of the formula (VI), because, at a pH below 7, the aldehyde groups in the ortho-position to the phenolic hydroxyl are oxidized more rapidly than the aldehyde group in the para-position. It therefore becomes possible to selectively oxidize the former while avoiding, or at least greatly limiting, the oxidation of the latter.

In this case, the process according to the invention makes it possible to obtain 3,4-dihydroxy or 3,4,5-trihydroxybenzaldehydes, which are intermediates in great demand in organic syntheses.

Among the hydroxybenzaldehydes to which the process according to the invention is advantageously applied, the following are exemplary: salicylaldehyde, p-hydroxybenzaldehyde, 2,3-dihydroxybenzaldehyde, 2,6-dihydroxybenzaldehyde, 2-hydroxy-3-methoxybenzaldehyde (ortho-vanillin), protocatechualdehyde, 2,4-diformylphenol, 2,6-diformylphenol, 1,2-dihydroxy-3,5-diformylbenzene, 1,2-dihydroxy-4,6-diformylbenzene, 1-hydroxy-2-methoxy-4,6-diformylbenzene (4,6-diformylguaiacol) and 1-hydroxy-2-ethoxy-4,6-diformylbenzene.

Among the polyhydroxybenzaldehydes which can be prepared via the process according to the present invention, the following are exemplary: protocatechualdehyde, ortho-hydroxy-para-vanillin, 3,4-dihydroxy-5-ethoxybenzaldehyde, 3,4,5-trihydroxybenzaldehyde, 3,4-dihydroxy-5-methoxybenzaldehyde and pyrogallol.

The process according to the invention is very particularly suitable for the oxidation of mixtures of vanillin and ortho-vanillin, but it is preferably used for the oxidation of 2,4-diformylphenol to protocatechualdehyde (3,4-dihydroxybenzaldehyde), diformylguaiacol to 3,4-dihydroxy-5-methoxybenzaldehyde, 2,6-dihydroxybenzaldehyde to pyrogallol, 4,6-diformyl-2-ethoxyphenol to 3,4-dihydroxy-5-ethoxybenzaldehyde, 1,2-dihydroxy-4,6-diformylbenzene to 3,4,5-trihydroxybenzaldehyde or 2,4,6-triformylphenol to 3,4,5-trihydroxybenzaldehyde.

The temperature at which the reaction is carried out can vary over wide limits. In general, temperatures of between 0° C. and the boiling point of the reaction medium are suitable. In the majority of cases, temperatures ranging from 10° to 100° C., and preferably from 30° to 80° C. are used.

The concentration of the hydroxybenzaldehyde suspended in the reaction medium is not critical and can also vary over wide limits. It can range from 0.1 to 10 mols per liter, and preferagly from 0.2 to 2 mols per liter. However, these limits can be exceeded without departing from the scope of the invention.

The amount of hydrogen peroxide, expressed in mols of $H_2O_2$ per aldehyde group to be oxidized, too can vary over wide limits. Thus, it is possible to carry out the reaction with a deficiency or an excess of hydrogen peroxide, relative to the theoretical amount. In general, amounts of hydrogen peroxide which are close to the stoichiometry of the reaction are used, namely, approximately 1 mol of $H_2O_2$ per aldehyde group to be oxidized. In the case of hydroxybenzaldehydes containing only one aldehyde group, whether this be in the ortho- or para-position, or containing two aldehyde groups in the ortho-position, it is possible to use a large excess of hydrogen peroxide, but this does not afford any particular advantage. If hydroxybenzaldehydes containing both an aldehyde group in the para-position and one or two groups in the ortho-position are oxidized, it is preferable to limit the excess of hydrogen peroxide relative to the stoichiometric amount for the oxidation of the aldehyde groups in the ortho-position. In practice, it is advantageous in this case to use an amount of hydrogen peroxide of at most 1.6 mols per aldehyde group in the ortho-position. It is also possible to carry out the reaction with a deficiency of hydrogen peroxide, but in this case the degree of conversion of the starting hydroxybenzaldehyde is limited. Briefly, an amount of hydrogen peroxide ranging from 0.5 to 1.8 mols of $H_2O_2$ per aldehyde group to be oxidized is suitable; preferably, such amount ranges from 1 to 1.5.

The concentration of the aqueous hydrogen peroxide solution is not critical. For practical reasons, the usual solutions having a concentration of between 20 and 75% by weight are used.

Among the alkali metal or alkaline earth metal bases which are useful in carrying out the subject process, exemplary are the hydroxides, such as sodium hydroxide, potassium hydroxide, lithium hydroxide and barium hydroxide; alkali metal alkanolates, such as sodium or potassium methylate, ethylate, isopropylate and t-butylate; sodium or potassium carbonates or bicarbonates; and, in general, the salts of alkali metal or alkaline earth metal bases with weak acids.

The amount of alkali metal base utilized is calculated such that the pH of the medium is below the limiting value defined above. It is determined by the pKa, in water, of the hydroxybenzaldehyde subjected to oxidation.

The process according to the present invention is preferably carried out under an inert gas atmosphere, such as a nitrogen or argon atmosphere.

The polyphenols obtained by the oxidation of hydroxybenzaldehydes via the process according to the invention can be separated from the reaction medium employing conventional techniques. For example, it is possible to treat the oxidation medium with an alkali metal base in order to completely saponify the phenyl formate formed, such as to liberate the phenol, and then separate the latter by art recognized technique, for example, by extraction.

If the product obtained is destined for the preparation of other derivatives, it can be advantageous not to separate off the polyphenol obtained, but to use the reaction mixture directly for the subsequent operation. Thus, if it is desired to prepare ethers derived from the product polyphenols, by alkylation with an alkylating agent, such as alkyl halides and sulfates, in an alkaline medium, it is possible to add a sufficient amount of an alkali metal base, such as those mentioned above, to the crude oxidation medium in order to bring the pH to a value above 8, and then carry out the alkylation reaction under the customary conditions. A process of this type can be used, in particular, for the etherification of the polyhydroxybenzaldehydes of the formula (VII). Thus, by carrying out the oxidation step and etherification step in succession, it is possible to prepare trimethoxybenzaldehyde from diformylguaiacol.

The hydroxybenzaldehydes of the formula (I) to which the process according to the invention can be applied are generally known products, with the exception of 2,4,6-triformylphenol, which has not been described in the literature, and same can be prepared by various methods of organic synthesis.

Thus, hydroxybenzaldehydes can be prepared by the oxidation of methylolphenols with molecular oxygen or a gas which contains molecular oxygen, in an alkaline aqueous phase, in the presence of a catalyst based on a noble metal such as platinum and palladium, optionally containing, as an activator, metals such as cadmium, cerium, bismuth, lead, silver, tellurium or tin. Processes of this type are described in U.S. Pat. No. 3,673,257, French Pat. No. 75/09,932, published under No.

2,305,420, and French Patent Application No. 77/13,941, published under No. 2,350,323.

Insofar as the methylolphenols are concerned, most of these are known products which can be prepared by the hydroxymethylation of substituted or unsubstituted phenols with formaldehyde or compounds which generate formaldehyde, such as paraformaldehyde, under the most diverse conditions (compare, in particular, H. G. Peer, *Rec. Trav. Chim. Pays-Bas,* 79, 825–835 (1960); British Pat. No. 774,695; British Pat. No. 751,845; European Patent Application No. 165; J. H. Freeman, *J. Amer. Chem. Soc.,* 74 6257–6260 (1952), and 76, 2080–2087 (1954); H. G. Peer, *Rec. Trav. Chim. Pays-Bas,* 78, 851–863 (1959); H. Euler et al, *Arkiv fur Chem.,* 13, 1–7 (1939); and P. Claus et al, *Monath. Chem.,* 103, (1178–1193 (1972)).

A process for the hydroxymethylation of phenols which is very especially suitable for the synthesis of the methylolphenols which can be used for the preparation of hydroxybenzaldehydes consists of condensing formaldehyde, or compounds which generate formaldehyde, with a phenol, in the aqueous phase, in the presence of an alkali metal base or alkaline earth metal base.

It appears to be particularly advantageous from an industrial point of view, for carrying out the process according to the present invention, to use hydroxybenzaldehydes obtained by a two-step process comprising (a) the hydroxymethylation of a phenol, in an aqueous medium, in the presence of an alkali metal base or alkaline earth metal base, with formaldehyde or a compound which generates formaldehyde, to give a mono- or poly-methylolphenol, and (b) the oxidation, without intermediate separation, of the methylolphenols with molecular oxygen or a gas which contains molecular oxygen, in an alkaline aqueous phase, in the presence of a palladium or platinum catalyst optionally containing, as an activator, a metal such as those noted hereinabove.

The process of the invention is applied with marked success to hydroxybenzaldehydes of the formula (I) obtained by a two-step process comprising:

(1) the hydroxymethylation of phenols having the structural formula:

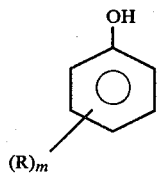

(VIII)

which are unsubstituted in at least one of the ortho-positions to the phenolic hydroxyl and, if appropriate, in the paraposition, to yield methylolphenols having the structural formula:

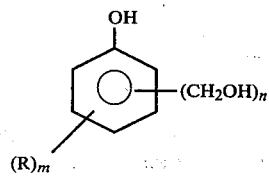

(IX)

which contain at least one methylol group in the ortho- and/or para-position to the hydroxyl group, with formaldehyde or a formaldehyde generator, in the aqueous phase, in the presence of an alkali metal base or alkaline earth metal base;

(2) the oxidation, in an alkaline aqueous phase, of the methylolphenols of the formula (IX) resulting from the first step, with molecular oxygen or a gas which conains molecular oxygen, in the presence of a palladium or platinum catalyst optionally containing, as an activator, a metal such as those used in the prior art, without intermediate separation of the methylolphenols.

Even more specifically, the process according to the present invention is well adapted for the preparation of the polyphenols containing an aldehyde group, of the formula (VII), from hydroxybenzaldehydes of the formula (VI) obtained by a process comprising the hydroxymethylation of the phenols of the formula (VIII), in the aqueous phase, in the presence of an alkali metal base or alkaline earth metal base, to yield polymethylolphenols having the structural formula:

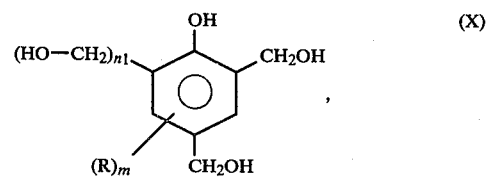

(X)

with formaldehyde or a compound which generates formaldehyde, followed, without separation, by the oxidation, in an alkaline aqueous phase, of the polymethylolphenols of the formula (X), with molecular oxygen or a gas which contains molecular oxygen, in the presence of a palladium-based or platinum-based catalyst optionally containing a customary activating metal.

It is particularly advantageous from an industrial point of view to combine the process for the oxidation of the hydroxybenzaldehydes according to the present invention with the two steps for the preparation of the starting hydroxybenzaldehydes by the hydroxymethylation of a phenol with formaldehyde, in the aqueous phase, followed by oxidation with oxygen, in an alkaline aqueous phase, in the presence of a platinum or palladium catalyst. In fact, because of the similarity of the reaction media in each of the three steps, it is not necessary to separate the intermediates upon completion of each step, and it is thus possible to transform very simply from the initial phenols to the final polyphenols or polyhydroxybenzaldehydes. During the stage of hydroxymethylation of the starting phenol, various methylolphenols which differ from one another in the number and/or the position of the methylol groups can be formed, depending on the reaction conditions, and it is not necessary to separate these methylolphenols from one another; the mixture of the different mono- and/or poly-methylolphenols thus obtained is then directly subjected to oxidation with molecular oxygen to produce a mixture of mono- or polyformylphenols which can be oxidized directly by the process according to the invention. Thus, starting from phenol, it is possible to obtain, by hydroxymethylation, ortho-hydroxybenzyl alcohol, para-hydroxybenzyl alcohol, 2,6-bis-hydroxymethylphenol, 2,4-bis-hydroxymethylphenol and 2,4,6-tri-hydroxymethylphenol, typically in the form of mixtures of two or more of these compounds which contain a greater or lesser proportion of each of the latter, depending upon the reaction conditions. In the same manner, starting from guaiacol, it is possible to obtain mixtures containing two or three of the following hydroxymethylmethoxyphenols: 2-methoxy-4-hydroxymethylphenol, 2-methoxy-6-hydroxymethylphenol and 2-methoxy-4,6-bishydroxymethylphenol.

By oxidation with molecular oxygen, mixtures of hydroxybenzaldehydes will be obtained which contain two or more of the following aldehydes: salicylaldehyde, p-hydroxybenzaldehyde, 2,4-diformylphenol, 2,6-diformylphenol and 2,4,6-triformylphenol, starting from phenol or alternatively 2-hydroxy-3-methoxybenzaldehyde, vanillin and 2-methoxy-4,6-diformylphenol, starting from guaiacol.

The conditions selected for carrying out the steps of hydroxymethylation and oxdation of the methylolphenols are those reported in the prior art referred to hereinabove.

In general, the hydroxymethylation step is carried out at a temperature ranging from 0° to 100° C. and preferably from 20° to 70° C.; the molar ratio formaldehyde/phenol governs the nature of the hydroxymethylphenols obtained and consequently that of the final polyphenols; this ratio can range from 0.1/1 to 4 and preferably from 0.8 to 4.

The amount of base present in the hydroxymethylation medium, expressed as the number of mols of base/phenolic hydroxyl of the phenol to be hydroxymethylated, can vary over wide limits. In general, this ratio, which is variable according to the nature of the base, can range from 0.1 to 2 and preferably from 0.5 to 1.1. As the base, it is possible to use those mentioned above for the oxidation stage with hydrogen peroxide. The use of alkali metal hydroxides (especially potassium hydroxide and sodium hydroxide) in aqueous solution is particularly convenient.

The formaldehyde can be used in the form of an aqueous solution, the concentration of which is not critical. This concentration can range from 20 to 50% by weight; it is preferred to use the commercially available solutions having a concentration of about 30 to 40% by weight.

Among the phenols of the formula (VIII) which can be used as starting materials for the synthesis of polyphenols, and more especially polyhydroxybenzaldehydes, exemplary are phenol, hydroquinone, pyrocatechol, guaiacol, 2-ethoxyphenol, 2-propoxy-orthocresol, 3-methoxyphenol, 3-ethoxyphenol, 3-isopropoxyphenol, 3-t-butoxyphenol, m-cresol, ortho-cresol and para-cresol.

The oxidation of the methylolphenols to intermediate hydroxybenzaldehydes with molecular oxygen can be carried out, as indicated above, directly upon the aqueous alkaline solution of the salts of the methylolphenols obtained in the hydroxymethylation step. If necessary, the pH of the solution is adjusted to a value ranging from 8 to 13 by the addition of an alkali metal base of alkaline earth metal base. The optimum value of the pH depends upon the nature of the methylolphenols.

The catalysts employed for this oxidation step can be selected from among those described in U.S. Pat. No. 3,673,257, French Pat. No. 75/09,932 and French Patent Application No. 77/13,941, mentioned above. It is preferred to use platinum and/or palladium catalysts selected from any of the available forms (platinum black, palladium black, platinum metal or palladium metal) and preferably deposited on an inert support, such as carbon black, active charcoals, silica, asbestos or alumina. The activator can be selected from among all of those indicated in the immediately above-mentioned patents or patent applications. It is preferred to use bismuth, lead and cadmium in the form of free metals or in the form of cations. In the latter case, the associated anion is not critical and it is thus possible to use any derivatives of these metals. It is preferred to use bismuth metal or its derivatives.

The following are exemplary preferred activators: bismuth oxides; bismuth hydroxides; salts of mineral hydracids, such as: bismuth chloride, bromide, iodide, sulfide, selenide and telluride; salts of mineral oxyacids, such as: bismuth sulfite, sulfate, nitrite, nitrate, phosphite, phosphate, pyrophosphate, carbonate, perchlorate, antimonate, arsenate, selenite and selenate; and salts of oxyacids derived from transition metals, such as: bismuth vanadate, niobate, tantalate, chromate, molybdate, tungstate and permanganate.

Other suitable compounds are salts of aliphatic or aromatic organic acids, such as: bismuth acetate, propionate, benzoate, salicylate, oxalate, tartrate, lactate and citrate; and phenates such as: bismuth gallate and pyrogallate. These salts and phenates can also be bismuthyl salts.

Other inorganic or organic compounds which can be used are binary combinations of bismuth with elements such as phosphorus and arsenic, heteropolyacids containing bismuth, and also their salts; aliphatic and aromatic bismuthines are also suitable.

Specific examples are:

(i) as oxides: BiO; $Bi_2O_3$; $Bi_2O_4$; and $Bi_2O_5$;

(ii) as hydroxides: $Bi(OH)_3$;

(iii) as salts of mineral hydracids: bismuth chloride, $BiCl_3$; bismuth bromide, $BiBr_3$; bismuth iodide, $BiI_3$; bismuth sulfide, $Bi_2S_3$; bismuth selenide, $Bi_2Se_3$; and bismuth telluride, $Bi_2Te_3$;

(iv) as salts of mineral oxyacids: basic bismuth sulfite, $Bi_2(SO_3)_3.Bi_2O_3.5H_2O$; neutral bismuth sulfate, $Bi_2(SO_4)_3$; bismuthyl sulfate, $(BiO)HSO_4$; bismuthyl nitrite, $(BiO)NO_2.0.5H_2O$; neutral bismuth nitrate, $Bi(NO_3)_3.5H_2O$; bismuth magnesium nitrate, $2Bi(NO_3)_3.3Mg(NO_3)_2.24H_2O$; bismuthyl nitrate, $(BiO)NO_3$; bismuth phosphite, $Bi_2(PO_3H)_3.3H_2O$; neutral bismuth phosphate, $BiPO_4$; bismuth pyrophosphate, $Bi_4(P_2O_7)_3$; bismuthyl carbonate, $(BiO)_2CO_3.0.5H_2O$; neutral bismuth perchlorate, $Bi(ClO_4)_3.5H_2O$; bismuth antimonate, $BiSbO_4$; neutral bismuth arsenate, $Bi(AsO_4)_3$; bismuthyl arsenate, $(BiO)AsO_4.5H_2O$; bismuth selenite, $Bi_2(SeO_3)_3$; bismuth vanadate, $BiVO_4$; bismuth niobate, $BiNbO_4$; bismuth tantalate, $BiTaO_4$; neutral bismuth chromate, $Bi_2(CrO_4)_3.3.5H_2O$; neutral bismuthyl chromate, $(BiO)_2CrO_4$; bismuthyl dichromate, $(BiO)_2Cr_2O_7$; acid bismuthyl chromate, $H(BiO)CrO_4$; potassium bismuthyl chromate, $K(BiO)Cr_3O_{10}$; bismuth molybdate, $Bi_2(MoO_4)_3$; bismuth tungstate, $Bi_2(WO_4)_3$; sodium bismuth molybdate, $NaBi(MoO_4)_2$; and basic bismuth permanganate, $Bi_2O_2(OH)MnO_4$;

(v) as salts of aliphatic or aromatic organic acids: bismuth acetate, $Bi(C_2H_3O_2)_3$; bismuthyl propionate, $(BiO)C_3H_5O_2$; basic bismuth benzoate, $C_6H_5CO_2Bi(OH)_2$; bismuthyl salicylate, $C_6H_4CO_2(BiO)(OH)$; bismuth oxalate, $(C_2O_4)_3Bi_2$; bismuth tartrate, $Bi_2(C_4H_4O_6)_3.6H_2O$; bismuth lactate, $(C_6H_9O_5)OBi.7H_2O$; and bismuth citrate, $C_6H_5O_7Bi$;

(vi) as phenates: basic bismuth gallate, $C_7H_7O_7Bi$; and basic bismuth pyrogallate, $C_6H_3(OH)_2(OBi)(OH)$.

The following are additional examples of suitable inorganic or organic compounds: bismuth phosphide; bismuth arsenide, $Bi_3As_4$; sodium bismuthate, $NaBiO_3$; bismuth-thiocyanic acids, $H_2[Bi(CNS)_5]$ and $H_3[Bi(CNS)_6]$, and their sodium and potassium salts;

trimethylbismuthine, Bi(CH$_3$)$_3$; and triphenylbismuthine, Bi(C$_6$H$_5$)$_3$.

The bismuth derivatives which are preferably used are: bismuth oxides; bismuth oxides; bismuth hydroxides; bismuth salts or bismuthyl salts of mineral hydracids; bismuth salts or bismuthyl salts of mineral oxyacids; bismuth salts or bismuthyl salts of aliphatic or aromatic organic acids; and bismuth phenates or bismuthyl phenates.

A group of activators which are particularly suitable consists of: bismuth metal; bismuth oxides, Bi$_2$O$_3$ and Bi$_2$O$_4$; bismuth hydroxide, Bi(OH)$_3$; neutral bismuth sulfate, Bi$_2$(SO$_4$)$_3$; bismuth chloride, BiCl$_3$; bismuth bromide, BiBr$_3$; bismuth iodide, BiI$_3$; neutral bismuth nitrate, Bi(NO$_3$)$_3$.5H$_2$O; bismuthyl carbonate, (BiO)$_2$CO$_3$.O.5H$_2$O; bismuth acetate, Bi(C$_2$H$_5$O$_2$)$_3$; and bismuthyl salicylate, C$_6$H$_4$CO$_2$(BiO)(OH).

The amount of activator used, expressed as the amount of metal contained in the activator, relative to the weight of the noble metal employed, can vary over wide limits. For example, this amount can be as small as 0.1% and can be as much as the weight of noble metal employed, or can even exceed this weight to no disadvantage.

The amount of catalyst to be used, expressed as the weight of platinum or palladium metal, relative to that of the hydroxymethylphenol, can vary from 0.01 to 4% and preferably from 0.04 to 2%.

The concentration by weight of the hydroxymethylphenol in the aqueous medium usually ranges from 1% to 60%, preferably from 2% to 30%.

If the polyphenols are prepared from a phenol by carrying out, in succession, the steps of hydroxymethylation and of oxidation with molecular oxygen and then with hydrogen peroxide, it is preferable, for reasons of convenience, to use the same base for adjusting the pH to the desired value in each step. It is preferred to use an alkali metal base, and in particular sodium hydroxide and potassium hydroxide.

In practice, one method of carrying out the oxidation of hydroxymethylphenol consists of bringing the aqueous solution containing the compound to be oxidized, the alkaline agent, the catalyst based on a noble metal, and the activator, into contact with molecular oxygen or a gas containing molecular oxygen. The reaction is carried out under atmospheric pressure, but it can also be carried out under superatmospheric pressure, if appropriate. The mixture is then stirred at the desired temperature until the amount of oxygen consumed corresponds to that which is required, under the reaction conditions, to convert the hydroxymethylphenol to hydroxybenzaldehyde. In general, the oxidation is carried out at a temperature of the order of 10° to 100° C., preferably 20° to 60° C. After cooling, the catalyst is separated from the reaction mixture, if necessary, for example, by filtration, and the pH of the reaction mixture is then adjusted to a value below 7 by adding appropriate amount of a mineral acid. The oxidation with hydrogen peroxide is then carried out as above outlined.

The process described above, in which the stages of hydroxymethylation, of oxidation with oxygen and of Dakin oxidation in an acid medium are carried out in succession, is very particularly suitable for the preparation of hydroxy-p-vanillin from guaiacol. A process of this type constitutes a further object of the present invention.

In this case, the hydroxymethylation step is carried out at a temperature which preferably ranges from 20° to 60° C. These limits could be exceeded, but this does not bring about any particular advantages. The ratio formaldehyde/guaiacol is generally selected to be close to the stoichiometric ratio, namely, approximately 2; values of between 2 and 4 are suitable. It is preferred to use formaldehyde/guaiacol ratios ranging from 2 to 2.7.

Although it is possible to use any alkali metal base or alkaline earth metal base during the hydroxymethylation of the guaiacol, an alkali metal hydroxide, such as sodium hydroxide or potassium hydroxide, is preferably used. The molar ratio alkali metal base/guaiacol is approximately that amount required to neutralize the phenol group, namely, approximately 1. However, the reaction can be carried out with a deficiency of base, or a slight excess, without resulting in major disadvantages. A molar ratio base/guaiacol ranging from 0.5 to 1.2 is very particularly suitable. The concentration of the reactants in the reaction medium is also not critical and can vary over wide limits. The conditions of oxidation of dihydroxymethylguaiacol to diformylguaiacol, with oxygen, in the presence of a nobel metal, are those which have been generally defined above. In practice, the reaction temperature is selected ranging from 30° to 60° C. The pH of the oxidation medium of the dihydroxymethylguaiacol is preferably equal to at least 11 and, more preferably, it ranges from 11.5 to 12. The concentration of the dihydroxymethylguaicolate in the aqueous phase can vary over wide limits. It is preferably calculated such as not to exceed the solubility limits of the diformylguaiacolate formed. The condensation stage and oxidation stage can be carried out in the same equipment after adjustment of the pH to the desired value and after addition of the selected catalyst. To carry out the following step of oxidation of the diformylguaiacol to hydroxy-p-vanillin, the catalyst is separated from the aqueous alkaline solution of diformylguaiacolate by decantation or filtration, and the pH of the medium is then adjusted to the desired value, which preferably ranges from 4 to 5, by adding a strong acid. The oxidation with hydrogen peroxide is then carried out under the general conditions defined above.

Although the oxidation stages with oxygen and with hydrogen peroxide can be carried out in direct succession, after simple adjustment of the pH, it has been found that it is preferable to precipitate the diformylguaiacol by acidification of the alkaline solution to pH 3 by adding a strong acid, such as sulfuric acid, and then to separate the precipitate from the aqueous acid phase by decantation and drawing-off, or filtration. The crude diformylguaiacol thus obtained is then dispersed in water and the pH of the suspension is adjusted to the desired value.

The process in which the stages of hydroxymethylation, of oxidation with oxygen and of Dakin oxidation in an acid medium are carried out in succession is also very particularly suitable for the preparation of 3,4,5-trihydroxybenzaldehyde, which is an intermediate in the synthesis of 3,4,5-trimethoxybenzaldehyde from phenol. A process of this type, which constitutes yet another object of the present invention, uses the hydroxymethylation of phenol to 2,4,6-trimethylolphenol, the oxidation of the trimethylolphenol to 2,4,6-triformylphenol, with oxygen, in an alkaline medium, and then the oxidation of the triformylphenol to 3,4,5-trihydroxybenzaldehyde, with hydrogen peroxide, at a pH which is less than or equal to 7. As indicated above, 2,4,6- triformylphenol is a novel compound and in this respect it too constitutes another object of the present invention.

In all cases, it is preferable to carry out the condensation step and the oxidation step with hydrogen peroxide under an inert gas atmosphere such as an argon or nitrogen atmosphere.

In order to further illustrate the present invention and the advantages thereof, the following specific examples are given, it being understood that same are intended only as illustrative and in nowise limitative.

EXAMPLE 1

36 ml of water and 3.30 g (18 mmols) of 98% pure diformylguaiacol were introduced, under an argon atmosphere, into a 100 cm$^3$ glass round-bottomed flask equipped with a stirrer, two dropping funnels, a thermometer, a heating device, an inert gas inlet and a glass electrode for monitoring the pH, and the pH was then adjusted to 4 by adding a 15% strength by weight aqueous solution of sodium hydroxide, contained in one of the two dropping funnels. The contents of the flask were heated to 55° C. and 2.53 g of a 31.5% strength by weight aqueous solution of H$_2$O$_2$ (23.4 mmols) were added gradually such as to maintain the temperature at 50°-55° C. As the reaction proceeded, the sodium hydroxide solution was added gradually such as to maintain the pH at its value of 4. The addition of the hydrogen peroxide was complete after 30 minutes; the reaction mixture was maintained at 50° C. for an additional 10 minutes and was then cooled to 20° C., and the products present in the aqueous phase were determined by high-pressure liquid chromatography.

The following results were obtained:

(i) diformylguaiacol: 0.13 g (degree of conversion: 96%);

(ii) yield of hydroxy-p-vanillin, relative to the diformylguaiacol converted: 94%; and (iii) yield of hydroxy-o-vanillin, relative to the diformylguaiacol converted: 6%.

EXAMPLES 2 to 5

The procedure of Example 1 was repeated, but the pH of the reaction medium was maintained at the values indicated below by using the appropriate amount of sodium hydroxide solution. The results obtained are recorded in the table below.

| EXAMPLE | pH | DC of DFG[1] % | Y of HPV[2] % | Reaction Time |
|---|---|---|---|---|
| 2 | 7 | 90 | 70 | 40 minutes |
| 3 | 6 | 95 | 77 | 40 minutes |
| 4 | 4.7 | 96 | 90 | 40 minutes |
| 5 | 3.2 | 76 | 92 | 1 hour |

[1]degree of conversion of the diformylguaiacol;
[2]yield of hydroxy-p-vanillin, relative to the diformylguaiacol converted.

By way of comparison, Example 1 was repeated, the pH being maintained at values above 7; the following results were obtained.

| EXPERIMENT | pH | DC of DFG | Y of HPV |
|---|---|---|---|
| A | 8 | 80 | 50 |
| B | 10 | 75 | 45 |
| C | 11 | 56 | 35 |
| D | 12 | 27 | 18.5 |

EXAMPLE 6

Using the apparatus described in Example 1 and repeating the same procedure, 20 mmols of 98% pure diformylguaiacol in 40 ml of water were oxidized, at 45° C., with 26 mmols of H$_2$O$_2$ in a 31.5% strength aqueous solution, the pH being maintained at 6.75 by adding a 25% strength by weight aqueous solution of sodium carbonate (16 mmols of Na$_2$CO$_3$ were added in total). The products present in the reaction mixture were then determined by high-pressure liquid chromatography. The degree of conversion of the diformylguaiacol was 89% and the yield of hydroxy-p-vanillin, relative to the diformylguaiacol converted, was 78%.

EXAMPLE 7

The procedure of Example 6 was repeated, but 20 mmols of H$_2$O$_2$ were introduced instead of 26 mmols. The degree of conversion of the diformylguaiacol was then 73% and the yield of hydroxy-para-vanillin, relative to the diformylguaiacol converted, was 88%.

EXAMPLE 8

50 ml of deaerated water and 6.91 g (50 mmols) of 97% pure protocatechualdehyde were introduced into the apparatus described in Example 1, which had been purged with argon, the pH was then adjusted to 6 by adding a 30% strength by weight aqueous solution of sodium hydroxide, and the temperature was raised to 45° C. 5.4 g of 31.5% strength by weight hydrogen peroxide (50 mmols) were then added dropwise, over the course of 1 hour, under an argon atmosphere. The pH and the temperature were maintained at the values indicated above. Stirring was continued for 30 minutes after the addition was complete, a sample of the reaction mixture was then taken and the products present therein were determined by high-pressure liquid chromatography. This was followed by the dropwise addition of an additional amount of 2.6 g of hydrogen peroxide (24 mmols) and of 30% strength by weight sodium hydroxide solution, in order to maintain the pH and the temperature at the initial values. The products present were then determined again. The amounts of sodium hydroxide solution used in each of the two stages of the experiment were respectively 5.2 g and 1.2 g.

By way of comparison, the same experiment was repeated at pH=8 and pH=9. The results obtained are recorded in the following table:

| EXAMPLE | pH | H$_2$O$_2$, % of theory | 30% strength SODIUM HYDROXIDE SOLUTION g | TIME | PCA* g | DC* % | 1,2,4-THB* g | Y* % |
|---|---|---|---|---|---|---|---|---|
| 8 | 6 | 100 | 5.20 | 1 hour 30 minutes | 1.8 | 74 | 3.22 | 69 |
| EXPERIMENT | | 150 | 1.2 | 1 hour | 0.52 | 92.5 | 3.59 | 61.5 |

| EXAMPLE | pH | $H_2O_2$, % of theory | 30% strength SODIUM HYDROXIDE SOLUTION g | TIME | PCA* g | DC* % | 1,2,4-THB* g | Y* % |
|---|---|---|---|---|---|---|---|---|
| A | 8 | 100 | 6.9 | 1 hour | 1.8 | 74 | 1.61 | 34.5 |
|   |   | 150 | 2.2 | 45 minutes | 0.28 | 96 | 1.70 | 28 |
| B | 9 | 100 | 7.8 | 45 minutes | 2.7 | 61 | 0 | 0 |
|   |   | 150 | 2.7 | 30 minutes | 1.8 | 74 | 0 | 0 |

*PCA = protocatechualdehyde
*1,2,4-THB = 1,2,4-trihydroxybenzene
*DC = degree of conversion
*Y = yield relative to aldehyde converted.

EXAMPLE 9

40 ml of deaerated water and 4.56 g (32 mmols) of 2,3-dihydroxybenzaldehyde, having a purity of 97% by weight, were introduced into the apparatus described in Example 1, which had been purged with argon, and the pH was adjusted to 6 by adding a 30% strength by weight aqueous solution of sodium hydroxide. The contents of the flask were placed under an argon atmosphere and then heated to 45° C., and 3.45 g of a 31.5% strength by weight aqueous solution of hydrogen peroxide (32 mmols) were then gradually added, under stirring, such as to maintain the temperature at its initial value. The pH was maintained at the value of 6 by simultaneously adding 30% sodium hydroxide solution.

The addition of the hydrogen peroxide was complete after 35 minutes. The reaction mixture was maintained at 45° C. for an additional 30 minutes and then cooled to 30° C., and the products present in the aqueous phase were determined by high-pressure liquid chromatography. 3.2 g of 30% strength by weight aqueous solution of sodium hydroxide had been added in total. The temperature of the reaction mixture was then again raised to 45° C., an amount of 1.6 g (15 mmols) of 31.5% strength hydrogen peroxide was then added, the pH being maintained at the value of 6 by adding 30% strength by weight sodium hydroxide solution, and the procedure was then exactly as above.

By way of comparison, the same experiments were carried out, but the pH was adjusted to (A) 8 and (B) 10. The results of these various experiments are recorded in the following table:

|  | pH | $H_2O_2$, % of theory | 2,3-Dihydroxy-benzaldehyde g | DC % | Pyrogallol g | Y % |
|---|---|---|---|---|---|---|
| EXAMPLE |  |  |  |  |  |  |
| 9 | 6 | 100 | 0.66 | 85 | 3.4 | 99 |
|   |   | 150 | 0.04 | 99 | 4.04 | 100 |
| EXPERIMENT |  |  |  |  |  |  |
| A | 8 | 100 | 0.26 | 94 | 2.6 | 69 |
|   |   | 150 | 0 | 100 | 2.6 | 64 |
| B | 10 | 100 | 0.67 | 85 | 0.025 | 0.7 |
|   |    | 150 | 0.05 | 99 | 0.015 | 0.4 |

EXAMPLE 10

4.14 g of 97% pure protocatechualdehyde (30 mmols), 4.14 g of 97% pure 2,3-dihydroxybenzaldehyde (30 mmols) and 60 ml of deaerated water were introduced into the apparatus described in Example 1, which had been purged with argon.

The pH was adjusted to 5 by adding a 30% strength by weight aqueous solution of sodium hydroxide, and the temperature of the contents of the flask was then raised to 45° C. under an argon atmosphere. 5.18 g of 31.5% strength by weight hydrogen peroxide (48 mmols) were then gradually added, under vigorous stirring. The addition was conducted for 50 minutes. Stirring was maintained for 30 minutes after the addition of hydrogen peroxide was completed, and a sample of reaction mixture was then taken for determination of the products present by liquid phase chromatography.

The reaction was continued by adding 4.43 g of hydrogen peroxide (41 mmols) and sodium hydroxide solution, the temperature and the pH being maintained at the initial values. A further sample of reaction mixture was taken for determination of the products present by liquid phase chromatography.

By way of comparison, the same experiment was repeated at pH 9, using molar ratios $H_2O_2$/total number of aldehyde groups of 0.8 and 1.5, respectively.

The results of these various experiments are recorded in the following table:

|  | pH | $H_2O_2$, % of theory | PCA* g | DC | 1,2,4-THB* g | Y | DHBZ* g | DC | PY* g | Y |
|---|---|---|---|---|---|---|---|---|---|---|
| EXAMPLE |  |  |  |  |  |  |  |  |  |  |
| 10 | 5 | 80 | 2.53 | 39 | 0.70 | 47.5 | 0.79 | 81 | 2.67 | 87 |
|    |   | 150 | 1.49 | 64 | 0.80 | 33 | 0.08 | 98 | 2.89 | 78 |
| EXPERIMENT |  |  |  |  |  |  |  |  |  |  |
| A | 9 | 80 | 2.9 | 30 | 0.05 | 4 | 0.12 | 97 | 2.06 | 56 |
|   |   | 150 | 1.12 | 73 | 0.14 | 5 | 0 | 100 | 1.40 | 37 |

*PCA = protocatechualdehyde
*1,2,4-THB = 1,2,4-trihydroxybenzene
*DHBZ = 2,3-dihydroxybenzaldehyde
*PY = pyrogallol

EXAMPLE 11

3.13 g of 97% pure ortho-vanillin (20 mmols), 3.07 g of 99% pure para-vanillin (20 mmols) and 80 ml of deaerated water were introduced into the apparatus described in Example 1, which had been purged with argon.

The pH was adjusted from 3.1 to 6 by adding a 30% strength by weight aqueous solution of sodium hydroxide.

The temperature was adjusted to 50° C. and 2.16 g of 31.5% strength by weight hydrogen peroxide (20 mmols) were then dropwise added, under argon. The light-colored heterogeneous solution gradually darkened and became homogeneous when the addition was complete. Stirring was maintained for 20 minutes and a sample of reaction mixture was then taken for determination of the products present by liquid phase chromatography.

An amount of 31.5% strength hydrogen peroxide representing 25 mol % of the sum of the ortho-vanillin and para-vanillin introduced initially (namely, 10 mmols) was then added and the procedure was then exactly as above.

By way of comparison, the above experiment was repeated, the reaction being carried out at a pH of 9.75 and using molar ratios hydrogen peroxide/ortho-vanillin+para-vanillin of 0.5 and 0.75, respectively.

The results obtained are recorded in the following table:

|  | pH | $H_2O_2$, of theory | OV* g | OV* DC % | 3-MPC* g | 3-MPC* Y % | PV* g | PV* DC % | 2-MHQ* g | 2-MHQ* Y % |
|---|---|---|---|---|---|---|---|---|---|---|
| EXAMPLE 11 | 6 | 50 | 0.82 | 73 | 2.02 | 99 | 2.53 | 17 | 0.46 | 97 |
|  |  | 75 | 0.12 | 96 | 2.69 | 100 | 2.10 | 31 | 0.84 | 97 |
| EXPERIMENTS A | 9.75 | 50 | 0.61 | 80 | 1.95 | 87 | 2.58 | 15 | 0 | 0 |
|  |  | 75 | 0 | 100 | 2.49 | 89 | 2.31 | 24 | 0.07 | 10 |

*OV = ortho-vanillin
*3-MPC = 3-methoxypyrocatechol
*PV = para-vanillin
*2-MHQ = 2-methoxyhydroquinone

EXAMPLE 12

3.65 g of salicylaldehyde (30 mmols), 3.65 g of p-hydroxybenzaldehyde (30 mmols) and 60 ml of deaerated water were introduced into the apparatus described in Example 1, which had been purged with argon.

The pH of the contents of the flask was adjusted from 3.8 to 5 by adding a 30% strength by weight aqueous solution of sodium hydroxide, under an argon atmosphere, and the temperature was then adjusted to 50° C. 4.86 g of 31.5% strength by weight hydrogen peroxide (45 mmols) were then added over the course of 25 minutes. Stirring was maintained for 2 hours after the addition was completed, the pH was then adjusted to 5.5 and the reaction mixture was cooled to 25° C. and extracted 4 times with 100 ml of ethyl acetate. The various extracts were combined and the products present were then determined on a sample by vapor phase chromatography. By way of comparison, the above experiment was repeated, but the reaction was carried out at pH 9. The results are recorded in the following table:

|  | pH | $H_2O_2$, % of theory | DC of SA* | Y of PC* | DC of PHB* | Y of HQ* |
|---|---|---|---|---|---|---|
| EXAMPLE 12 | 5.5 | 75 | 76 | 99 | 58 | 85 |
| EXPERIMENT A | 9 | 75 | 98 | 80 | 33 | 70 |

*SA = salicylaldehyde
*PHB = para-hydroxybenzaldehyde
*PC = pyrocatechol
*HQ = hydroquinone

EXAMPLE 13

(1) Preparation of dihydroxymethylguaiacol 49 g of a 11.2% strength by weight aqueous solution of sodium hydroxide and 0.14 mol of guaiacol were introduced, under an argon atmosphere, into a 5-necked glass reactor equipped with a stirring system, a reflux condenser, a dropping funnel and a thermometer.

The temperature of the aqueous solution of sodium guaiacolate was maintained at 40° C., 0.35 mol of formaldehyde, in the form of a 30% strength by weight aqueous solution, was then added dropwise and the reaction mixture was stirred for 4 hours 30 minutes under these conditions.

A sample of the medium was then taken for determination of the formaldehyde by potentiometry, after oxime formation, and of the guaiacol and the products formed by high-pressure liquid chromatography.

The results obtained were as follows:

| Degree of conversion: | |
|---|---|
| guaiacol | 100% |
| formaldehyde | 74% |
| Yields relative to the guaiacol: | |
| 4,6-dihydroxymethylguaiacol | 80.5% |
| ortho-vanillyl alcohol (2-methoxy-6-hydroxymethylphenol) | 3% |
| p-vanillyl alcohol (2-methoxy-4-hydroxymethylphenol) | 1.5% |
| bis-(hydroxy-methoxy-hydroxymethylphenyl)-methane | 15.5% |

(2) Preparation of diformylguaiacol 193 g of distilled water, 60 mg of bismuth sulfate and 1 g of a platinum-based catalyst deposited on carbon black (namely, 50 mg of platinum) were introduced into the reactor described above, which contained the reaction mass obtained and was equipped with an electrode, a gas inlet consisting of a dip tube connected to an oxygen supply under a pressure of 1 bar, and a sodium hydroxide solution inlet coupled to a pH regulator. The temperature of the contents of the flask was raised to 45° C. and oxygen was then cahrged in, the pH being maintained at a value of 11.8 by adding 30% strength by weight sodium hydroxide solution. It was found that the reaction ceased after 6 hours under these conditions.

An aliquot of the reaction mixture was removed for determination of the products present by high-pressure liquid chromatography.

The following results were obtained:

| | |
|---|---|
| Degree of conversion of the 4,6-dihydroxymethylguaiacol | 100% |
| Yields relative to the guaiacol introduced in the first step: | |
| 4,6-diformylguaiacol (2-hydroxy-3-methoxyisophthalaldehyde) | 74% |
| ortho-vanillin | 1.3% |
| para-vanillin | 1.5% |

The yield of diformylguaiacol, relative to the 4,6-dihydroxymethylguaiacol formed in the previous step, was 92%.

(3) Preparation of hydroxy-para-vanillin

The crude oxidation solution resulting from the previous step was filtered under a nitrogen atmosphere in order to remove the catalyst. 300 ml of filtrate containing:

| | |
|---|---|
| diformylguaiacol | 100 mmols |
| ortho-vanillin and para-vanillin | 2 mmols | were collected.

The filtrate was deoxygenerated by passing nitrogen through, and its pH was then lowered from 11.8 to 4.3 by adding a 95% strength by weight aqueous solution of sulfuric acid. The temperature was then adjusted to 50° C. and 14.2 g of 30% strength by weight hydrogen peroxide (125 mmols), preliminarily deoxygenated, were then dropwise added, under an inert atmosphere and under vigorous stirring, the pH being maintained at 4 by simultaneously adding 30% strength by weight sodium hydroxide solution (13.3 g), which had also been deoxygenated. The addition lasted 2 hours, 30 minutes.

After the addition of hydrogen peroxide was complete, these conditions were maintained for an additional 30 minutes. The products present in the reaction mixture were determined by gas phase chromatography. The following results were obtained:

| | |
|---|---|
| Degree of conversion of the diformylguaiacol | 99.5% |
| Yield of hydroxy-para-vanillin, relative to the diformylguaiacol introduced | 89% |
| Yield of hydroxy-ortho-vanillin, relative to the diformylguaiacol introduced | 3.5% |

EXAMPLE 14

Stage 1. Preparation of dihydroxymethylguaiacol 221.2 g of a 30.5% strength by weight aqueous solution of sodium hydroxide and 1,000 g of distilled water were introduced, under stirring, into a 2.5 liter stainless steel reactor which had a jacket for circulating water thermostatted at 50° C. and which was equipped with a dual-turbine stirrer (400 rpm) and baffles, a reflux condenser, an inert gas inlet consisting of a dip tube, two dropping funnels, a thermometer and a device for monitoring the pH, the reactor having been purged with nitrogen.

The temperature of the contents of the reactor was raised to 50° C. and was maintained at this value, and 207.7 g of guaiacol (1.673 mols) were then introduced. 340.1 g of a 30% strength by weight aqueous solution of formaldehyde were then gradually added over the course of 10 minutes, while a stream of nitrogen was passed into the reaction mixture. These conditions were maintained for 4 hours, 30 minutes after the addition of the formaldehyde had commenced. This yields 1,768.8 g of reaction mixture, from which an aliquot was removed under a nitrogen atmosphere for determination of the products present by high-pressure liquid chromatography. The following results were obtained:

| | |
|---|---|
| Degree of conversion of the guaiacol (2.07 g of unconverted guaiacol were determined in the reaction mixture) | 99% |
| Yield of dihydroxymethylguaiacol | 76% |
| Yield of para-vanillyl alcohol | 5% |
| Yield of ortho-vanillyl alcohol | 3% |
| Yield of bis-(3-methoxy-4-hydroxy-5-hydroxymethylphenyl)-methane | 14% |

Stage 2. Preparation of diformylguaiacol 1,263 g of the above reaction mixture were removed under a nitrogen atmosphere and introduced into a 3.2 liter pressure-resistant stainless steel reactor maintained under a nitrogen atmosphere. This reactor was equipped with a jacket for circulating water thermostatted at 40° C., a nitrogen inlet, an air inlet, a reflux condenser, a device for monitoring the pH, a thermometer, a dual-turbine stirring device (450 rpm) and baffles, the following having already been introduced into said reactor: 1,340 g of distilled water and 2.12 g of a catalyst based on platinum and bismuth oxide, deposited on carbon black and containing 6% by weight of platinum metal and 2% by weight of bismuth metal. The contents of the reactor were stirred and the pH was adjusted to 12 by adding a 30% strength by weight aqueous solution of sodium hydroxide at 40° C. The introduction of nitrogen was terminated and air was then introduced at a rate of 700 liters/hour (at normal temperature and pressure) and under an absolute pressure of 3 bars. The pH of the reaction mixture was maintained at 12 by periodically adding 30% strength by weight sodium hydroxide solution. After 7 hours under these conditions, the introduction of air was terminated and the reactor was degassed and purged with nitrogen. A sample of reaction mixture was then taken for determination of the products present by high-pressure liquid chromatography. The following results were obtained:

| | |
|---|---|
| Degree of conversion of the dihydroxy-methylguaiacol | 100% |
| Yield of diformylguaiacol/guaiacol introduced in stage 1 | 69% |
| Yield of diformylguaiacol/dihydroxy-methylguaiacol introduced in stage 2 | 91% |
| Yield of hydroxymethyl-3-vanillin/guaiacol introduced in stage 1 | 0.8% |
| Yield of hydroxymethyl-o-vanillin/guaiacol introduced in stage 1 | 0.7% |
| Yield of p-vanillin/guaiacol introduced in stage 1 | 4% |
| Yield of o-vanillin/guaiacol introduced in | 2% | stage 1
-continued

Stage 3. Preparation of hydroxy-p-vanillin 2,735 g of reaction mixture were obtained upon completion of the reaction. The contents of the reactor were decanted in order to separate the catalyst from the liquid phase, and the latter was drawn off under a nitrogen atmosphere. A 2,000 g aliquot thereof was removed and introduced into the reactor used in the first stage, which had been purged with nitrogen beforehand. The contents of the reactor were acidified by adding 370.3 g of 20% strength sulfuric acid, cooling being effected by circulating 20° C. water in the jacket. The pH was thus adjusted from 12 to 3.5, causing the precipitation of the diformylguaiacol. The temperature of the medium was then 25° C. The medium was decanted in order to separate the diformylguaiacol from the liquid phase, and 1,903 g of acid aqueous phase were drawn off. 694 g of water were then introduced, under stirring; the mixture was left to again separate out and 477 g of water were removed. The contents of the reactor were heated to 50° C., the pH was then adjusted to 4.5 by adding 30% strength by weight sodium hydroxide solution, and 73 g of a 35% strength by weight aqueous solution of hydrogen peroxide were then gradually introduced over the course of 43 minutes, while at the same time maintaining the pH at its initial value. These conditions were maintained for 1 hour, 30 minutes and the pH was then adjusted to 6.5 by adding sodium hydroxide solution. A sample of reaction mixture was taken for determination of the products present by high-pressure liquid chromatography. The following results were obtained:

| | |
|---|---|
| Yield of hydroxy-para-vanillin/diformylguaiacol introduced and present in the aliquot part of the reaction mixture used in this last stage | 90% |

EXAMPLE 15

Stage 1: Preparation of 2,4,6-trimethylolphenol 100 g of a 30% strength solution of formaldehyde in water (1.0 mol) and 23.5 g of phenol were mixed in a 250 ml glass conical flask fitted with a magnetic stirrer. The volume was adjusted to 125 ml with about 10 ml of water, and 10.2 g of sodium hydroxide pellets (0.25 mol) were then added, under stirring. The mixture was cooled with an ice bath such as not to exceed 30° to 40° C. When the temperature had dropped to 25° C., the flask was purged with argon, the stirring was terminated and the homogeneous solution was left to stand for 24 hours at ambient temperature (22° to 23° C.).

After this period, no more than 315 millimols of free formaldehyde were determined. The reaction mixture was then introduced into 800 ml of cold isopropanol, under stirring. The heterogeneous mixture was stirred for an additional 10 minutes and the copious pinkish-white precipitate was then filtered off on Büchner apparatus. The precipitate was rinsed with isopropanol and then with ether. It was dried in an oven at 40° C. under a pressure of 1 mm of mercury, and this provided 40 g of a powder in which the following were determined by NMR:

11.5 mol % of a sodium dimethylolphenate;
83 mol % of sodium, 2,4,6-trimethylolphenate;
5.5 mol % of the disodium salt of a tetramethylolbishydroxydiphenylmethane.

Stage 2. Oxidation of the methylols 23.4 g of freshly prepared, crude sodium trimethylolphenate, containing 0.10 mol of substrate, and 400 ml of water were introduced into a 500 ml five-necked round-bottomed flask fitted with a central stirrer, a glass double electrode for measuring the pH, a thermometer, a dropping funnel and a gas inlet. The apparatus was purged with argon.

1 g of 4.3% strength by weight platinum-on-charcoal and 60 mg of bismuth (III) sulfate were added. The apparatus, connected to an oxygen supply at atmospheric pressure, was then purged with pure oxygen; the stirring rate was adjusted to 1,050 rpm.

The temperature was raised to 45° C. and at the same time the pH was raised to 11.0 by introducing 30% strength by weight sodium hydroxide solution (12 g, i.e., 0.09 mol).

After 1 hour, 15 minutes, 3.8 liters of oxygen had been absorbed and no additional oxygen was consumed during the next 25 minutes (3.83 liters). The catalyst was filtered off hot on a glass frit of porosity 4, the solid was washed with water and the filtrate was cooled to about 10° C. The latter was cautiously acidified with sulfuric acid; a precipitate began to appear at about pH 8. The addition of acid was terminated when the pH reached 4 (17 ml of 25% strength by weight $H_2SO_4$ had been used). The yellow solid obtained was filtered off on a glass frit of porosity 3, washed with 10 ml of water, drained and dried at 30° C. under a pressure of 1 mm of mercury. This yielded 14.7 g of yellow powder. The yield of weight of crude material, essentially containing triformylphenol and oligomers, was 82%.

The desired purified compound was isolated from this crude product by preparative liquid chromatography in a yield of 18%, relative to the starging 2,4,6-trimethylolphenol, namely, 3.2 g.

This compound, which is not described in the literature, possessed the following characteristics:

Melting point under a pressure of 760 mm of mercury: 206° C.

Nuclear magnetic resonance spectrum: singlet (2H) at delta=10.30 ppm; singlet (1H) at delta=9.99 ppm; singlet (2H) at delta=8.52 ppm Infra-red spectrum: intramolecular hydrogen-bonded hydroxyl band at 3,100 cm$^{-1}$; aldehyde carbonyl band at 1,690 cm$^{-1}$ at 1,665 cm$^{-1}$; aromatic band at 1,595 and 1,460 to 1,445 cm$^{-1}$.

Mass spectrum: M: 178; M—CO=150; M—CHO=149; M—CO—CHO=121; M—2CO—CHO=93; M—3CO—CHO=65

2,4,6-Triformylphenol is insoluble in water at 25° C. and has the following solubilities in organic solvents at 25° C.

| | |
|---|---|
| ethanol | 0.5 g/liter |
| diethyl ether | 0.25 g/liter |
| benzene | 3 g/liter |

Stage 3. Oxidation of the triformylphenol with hydrogen peroxide at pH<7

450 mg of triformylphenol (2.5 mmols) were introduced into a 500 ml five-necked glass reactor fitted with a thermometer, an electrode, a condenser and two dropping funnels. 12.5 ml of deaerated water were added, the magnetic stirrer was started and the temperature was raised to 45° C., everything being carried out under nitrogen.

The pH was raised to 4.5 with 10% strength by weight sodium hydroxide solution contained in the first funnel, and 1.96 g of 10% strength by weight hydrogen peroxide (5.8 mmols) were then dropwise introduced, over the course of 10 minutes, from the second funnel.

The solution, which was heterogeneous at the beginning, gradually became homogeneous. The reaction mixture was maintained at 45° C. for:
50 minutes at pH 4.5, and
45 minutes at pH 5–5.5.
4.16 mmols of sodium hydroxide had been added in total.

Stage 4. Methylation of the 3,4,5-trihydroxybenzaldehyde

In order to more easily measure the yield of gallic aldehyde obtained during the previous step, all products obtained were methylated in the following manner:

In the apparatus described above, the dropping funnel containing 10% strength by weight sodium hydroxide solution was replaced by a funnel containing degassed 30% strength by weight sodium hydroxide solution. The funnel containing hydrogen peroxide was replaced by a funnel containing dimethyl sulfate (DMS).

The pH of the mixture was raised to 8, while maintaining a temperature of 45° C. and a nitrogen atmosphere. 4.75 g of DMS (37.5 mmols) were then introduced over a period of 40 minutes, while maintaining the pH at 8–8.5. The experiment was terminated when the pH stabilized, which was after 1 hour, the amount of 30% strength sodium hydroxide solution used then being 4.2 g (31.5 mmols).

After cooling to 20° C., the reaction mixture was acidified to pH 3.5 with 0.25 ml of 50% strength by weight $H_2SO_4$ and extracted three times with 20 ml of dichloroethane. The organic extracts were washed with 10 ml of water, dried over sodium sulfate and analyzed by gas phase chromatography.

The hydroxyls had been totally methylated because neither gallic aldehyde, nor 5-hydroxy-p-vanillin, nor seringaldehyde (3,5-dimethoxy-4-hydroxybenzaldehyde) and/or its isomer, 3,4-dimethoxy-5-hydroxybenzaldehyde, were observed.

| | |
|---|---|
| Yield of 3,4,5-trimethoxybenzaldehyde, relative to the triformylphenol introduced in step 3 | 216 mg = 44% |
| Yield of 1,3,4,5-tetramethoxybenzene | 24 mg = 5% |

The yield of gallic aldehyde was thus at least 44%, relative to the 2,4,6-triformylphenol introduced in step 3.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the preparation of optionally aldehyde substituted polyphenols by oxidizing, with hydrogen peroxide, a hydroxybenzaldehyde bearing at least one aldehyde substituent ortho- and/or para- to the nuclear hydroxyl group, in an aqueous reaction medium and in the presence of an alkali or alkaline earth metal base, the improvement comprising maintaining the pH of the said reaction medium in the range of from about 2 to 7 throughout the course of the oxidation reaction, with the hydrogen peroxide and an alkali metal base or alkaline earth metal base being added gradually to the reaction medium, whereby at least one formyl of the hydroxybenzaldehyde is oxidized to a hydroxyl.

2. The process as defined by claim 1, the starting material hydroxybenzaldehyde having the structural formula:

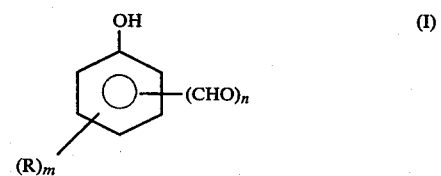

wherein n is an integer from 1 to 3, R represents an alkyl, alkoxy, hydroxyalkyl, cycloalkyl, aryl, alkoxyalkyl or hydroxyl, radical, a nitro group or a halogen atom, and m is an integer from 0 to 3, with the sum m+n being no greater than 4.

3. The process as defined by claims 1 or 2, wherein the product polyphenols have the structural formula:

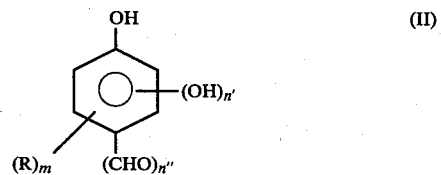

wherein n' is an integer from 1 to 2 and n" is 0 or 1, with the sum n'+n" being equal to n.

4. The process as defined by claim 3, wherein, in the formulae (I) and (II), R represents a lower alkyl radical, a lower alkoxy radical or a hydroxyl group.

5. The process as defined by claim 3, wherein n is equal to 2 or 3.

6. The process as defined by claim 5, wherein m is equal to 0 or 1.

7. The process as defined by claim 2, wherein polyphenols having the structural formula:

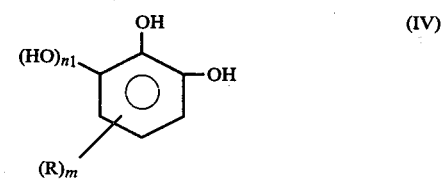

wherein $n_1$ is equal to 0 or 1, are prepared by oxidizing a hydroxybenzaldehyde having the structural formula:

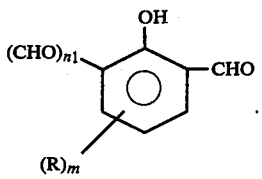  (III)

8. The process as defined by claim 2, wherein polyphenols containing two hydroxyl groups para- to each other are prepared by oxidizing a hydroxybenzaldehyde having the structural formula:

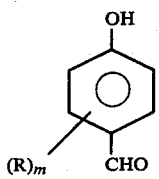  (V)

9. The process as defined by claims 7 or 8, comprising oxidizing mixtures of hydroxybenzaldehydes having the structural formulae (III) and (V).

10. The process as defined by claim 3, wherein a polyhydroxybenzaldehyde having the structural formula:

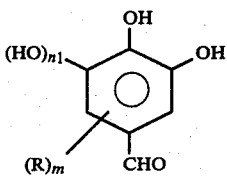  (VII)

wherein $n_1$ is equal to 0 or 1, is prepared by oxidizing a hydroxybenzaldehyde having the structural formula:

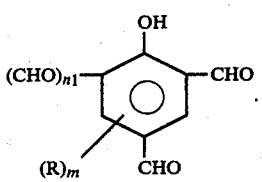  (VI)

11. The process as defined by claim 1, wherein 1,2,4-trihydroxybenzene is prepared by the oxidation of protocatechualdehyde.

12. The process as defined by claim 1, wherein pyrogallol is prepared by the oxidation of 2,3-dihydroxybenzaldehyde.

13. The process as defined by claim 1, wherein pyrogallol and 1,2,4-trihydroxybenzene are prepared by the oxidation of a mixture of protocatechualdehyde and 2,3-dihydroxybenzaldehyde.

14. The process as defined by claim 1, wherein 3-methoxyprocatechol and 2-methoxyhydroquinone are prepared by the oxidation of a mixture of ortho-vanillin and p-vanillin.

15. The process as defined by claim 1, wherein hydroquinone and pyrocatechol are prepared by the oxidation of a mixture of p-hydroxybenzaldehyde and salicylaldehyde.

16. The process as defined by claim 1, wherein 3,4-dihydroxy-5-methoxybenzaldehyde is prepared by the oxidation of 4,6-diformylguaiacol.

17. The process as defined by claim 1, wherein 3,4,5-trihydroxybenzaldehyde is prepared by the oxidation of 2,4,6-triformylphenol.

18. The process as defined by claims 1 or 2, the reaction being conducted at a temperature ranging from 0° to 100° C.

19. The process as defined by claims 1 or 2, wherein the amount of hydrogen peroxide, expressed in mols of $H_2O_2$ per aldehyde group to be oxidized, ranges from 0.5 to 1.8.

20. The process as defined by claims 1 or 2, wherein said base is a hydroxide, an alcoholate, or a salt of a weak acid with an alkali metal base.

21. The process as defined by claim 20, wherein the base is sodium hydroxide or potassium hydroxide.

22. The process as defined by claim 20, wherein the amount of base is determined such as to maintain the pH of the reaction medium at said value of no greater than 7.

23. The process as defined by claims 1 or 2, the pH of the reaction medium being maintained from 2 to 6.

24. The process as defined by claim 3, the hydroxybenzaldehyde oxidized having been obtained by a two-step process comprising (i) the hydroxymethylation of a phenol to mono- and/or poly-methylolphenols with formaldehyde or a formaldehyde generator, followed by (ii) the oxidation of the mono- and/or poly-methylolphenols with molecular oxygen or a gas which contains molecular oxygen, in an aqueous alkaline phase, in the presence of a catalyst comprising a noble metal, or a noble metal catalyst including an activator selected from the group comprising Cd, Ce, Bi, Pb, Ag, Te and Sn, or organic or inorganic derivatives thereof.

25. The process as defined by claim 24, wherein polyphenols having the structural formula:

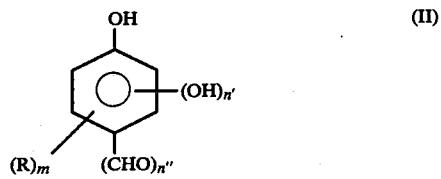  (II)

are prepared by (i) the hydroxymethylation of phenols having the structural formula:

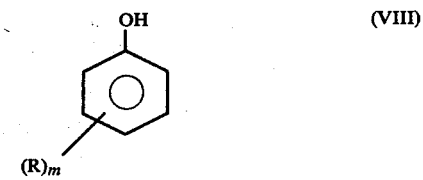  (VIII)

to yield hydroxymethylphenols having the structural formula:

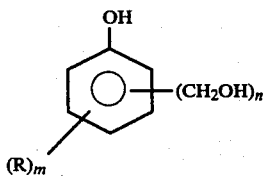

followed by (ii) the oxidation of the compounds (IX) with molecular oxygen, in an aqueous alkaline phase, to yield hydroxybenzaldehyde having the structural formula:

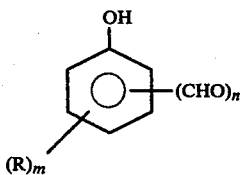

and thence (iii) the oxidation of the compounds (I) with hydrogen peroxide, in aqueous phase, at pH≦7.

26. The process as defined by claim 24, wherein polyhydroxybenzaldehyde having the structural formula:

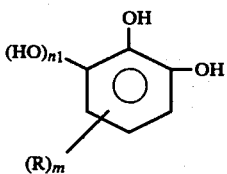

wherein $n_1$ is equal to 0 or 1, are prepared by (i) the hydroxymethylation of a phenol having the structural formula:

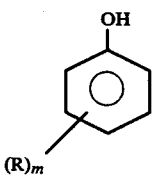

with formaldehyde or a formaldehyde generator, to yield poly-methylolphenols having the structural formula:

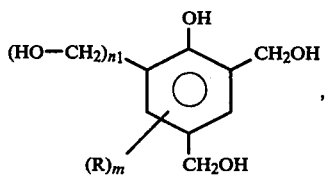

followed by (ii) oxidation of the compounds (I) with molecular oxygen, in an aqueous alkaline phase, to yield aldehydes having the structural formula:

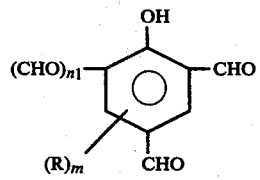

and thence (iii) the oxidation of the compounds (VI) with hydrogen peroxide, in aqueous phase, at pH≦7, in the presence of an alkali metal base or an alkaline earth metal base.

27. The process as defined by claim 24, wherein 3,4,5-trihydroxybenzaldehyde is prepared from phenol by (i) the hydroxymethylation of same to 2,4,6-trimethylolphenol, by (ii) the oxidation of said trimethylolphenol to 2,4,6-triformylphenol with oxygen, and by (iii) the oxidation of said 2,4,6-triformylphenol with hydrogen peroxide, in aqueous phase, at pH≦7, in the presence of an alkali or alkaline earth metal base.

28. The process as defined by claim 24, wherein 3,4-dihydroxy-5-methoxybenzaldehyde is prepared from guaiacol by (i) the hydroxymethylation of same to 4,6-dihydroxymethyl-2-methoxyphenol, by (ii) the oxidation of said dihydroxymethylguaiacol to diformylguaiacol with molecular oxygen, and by (iii) the oxidation of the diformylguaiacol with hydrogen peroxide, in aqueous phase, at pH≦7, in the presence of an alkali or alkaline earth metal base.

29. The process as defined by claim 24, wherein the hydroxymethylation is carried out in aqueous phase, in the presence of an alkali or alkaline earth metal base, at a temperature ranging from 0° to 100° C., the molar ratio formaldehyde/phenol being between 0.1 and 4.

30. The process as defined by claim 24, wherein the oxidation of the mono- and/or poly-methylolphenols with molecular oxygen is carried out in aqueous alkaline phase, at pH≧8, at a temperature of 10° to 100° C., in the presence of a catalyst comprising 0.01 to 4% by weight of platinum or palladium metal, relative to the methylolphenol, or such catalyst further comprising 0.2 to 100% by weight of an activator, relative to said noble metal.

31. The process as defined by claim 24, wherein the steps of (i) hydroxymethylation in aqueous phase, by oxidation of the mono- and/or poly-methylolphenols with molecular oxygen, in an aqueous alkaline phase, and of (ii) oxidation of the hydroxybenzaldehyde with hydrogen peroxide, in aqueous phase, at pH≦7, are carried out successively, without separation of the intermediates formed during the first two steps.

32. A process for the preparation of 3,4-dihydroxy-5-methoxybenzaldehyde as defined by claim 28, wherein: (i) in a first stage, dihydroxymethylguaiacol is prepared by reacting an aqueous solution of formaldehyde or a formaldehyde generator, with an aqueous solution of an alkali metal guaiacolate, at a temperature ranging from 20° to 60° C., the molar ratio formaldehyde/guaiacol ranging from 2 to 4 and the molar ratio alkali metal base/guaiacol ranging from 0.5 to 1.2; (ii) in a second stage, adding a platinum-based catalyst deposited on an inert support, or such catalyst/support further comprising an activator selected from the group comprising Cd, Ce, Bi, Pb, Ag, Te and Sn, or derivatives thereof, to the aqueous solution of alkali metal dihydroxymethylguaiacolate obtained in step (i), the alkali metal dihydroxymethylguaiacolate being oxidized to the alkali metal diformylguaiacolate with molecular oxygen or a gas which contains molecular oxygen, at a temperature ranging from 30° to 60° C., the pH of the medium ranging from 11.5 to 12, and the catalyst being then separated off; and (iii) in a third stage, the alkali metal diformylguaiacolate being oxidized by the gradual addition of hydrogen peroxide to the aqueous solution obtained in stage (ii), after adjustment of the pH to a value ranging from 4 to 5 by addition of strong acid, the temperature ranging from 30° to 80° C. and the pH being maintained from 4 to 5 with an alkali metal base, and the molar ratio hydrogen peroxide/alkali metal diformylguaiacolate ranging from 1 to 1.5.

33. The process as defined by claim 32, wherein the stages (i) and (iii) are carried out under an inert gas atmosphere.

34. The process as defined by claim 32, wherein, after removal of the catalyst upon completion of stage (ii), the alkaline solution of alkali metal diformylguaiacolate is acidified to a pH which is less than or equal to 3.5, to precipitate the diformylguaiacol, with the latter being separated from the aqueous phase and then suspended in water, the pH being adjusted to a value ranging from 4 to 5 and the oxidation being carried out with hydrogen peroxide.

35. The process as defined by claim 1, wherein an alkali metal base or alkaline earth metal base is added progressively so as to maintain the pH of the reaction medium in the range of from 3 to 6.

36. The process as defined by claim 1, wherein the pH of the reaction medium is maintained in the range of from 3 to 6.

* * * * *

UNITED STATES PATENT AND TRADEMARK OFFICE
CERTIFICATE OF CORRECTION

PATENT NO. : 4,435,601

DATED : March 6, 1984

INVENTOR(S) : Formanek et al

It is certified that error appears in the above-identified patent and that said Letters Patent is hereby corrected as shown below:

Title page, § 75, "LYONS" should read --LYON--.

Column 1, line 25, "protocatechaualdehyde" should be --protocatechualdehyde--.

Column 7, line 44, "preferagly" should be --preferably--.

Column 10, line 5, "conains" should be --contains--.

Column 11, line 13, "oxdation" should be --oxidation--.

Column 14, line 29, "dihydroxymethylguaicolate" should be --dihydroxymethylguaiacolate--.

Column 21, line 2, "cahrged" should be --charged--.

Column 27, line 61, "methoxyprocatechol" should be --methoxypyrocatechol--.

Signed and Sealed this

Twenty-sixth Day of March 1985

[SEAL]

Attest:

DONALD J. QUIGG

Attesting Officer

Acting Commissioner of Patents and Trademarks